(12) United States Patent
Ghosal

(10) Patent No.: US 6,362,167 B1
(45) Date of Patent: Mar. 26, 2002

(54) METHOD OF BLOCKING FREE RADICAL PROCESSES WHICH RESULT IN MEDIATED PATHOLOGY WITHOUT DELETERIOUS PRO-OXIDANT SIDE REACTIONS

(75) Inventor: Shibnath Ghosal, Varanasi (IN)

(73) Assignees: Natreon Inc., New Brunswick, NJ (US); Indian Herbs Research & Supply Company Ltd., Sharanpur (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/667,043

(22) Filed: Sep. 21, 2000

Related U.S. Application Data

(63) Continuation-in-part of application No. 09/251,917, filed on Feb. 17, 1999, now Pat. No. 6,124,268, and a continuation-in-part of application No. 09/503,899, filed on Feb. 15, 2000, now Pat. No. 6,235,721.

(51) Int. Cl.$^7$ ................................................ A01N 65/00
(52) U.S. Cl. ........................... 514/25; 514/27; 424/401; 424/439; 424/440; 426/72; 426/541; 426/542; 426/546; 426/655; 426/658
(58) Field of Search ..................... 514/25, 27; 424/769, 424/777, 401, 439, 440; 426/72, 541, 542, 546, 655, 658

(56) References Cited

U.S. PATENT DOCUMENTS 6,124,268 A * 9/2000 Ghosal ........................ 514/27

\* cited by examiner

Primary Examiner—Frederick Krass
(74) Attorney, Agent, or Firm—Walter Katz

(57) ABSTRACT

A method of blocking free radical processes in an animal which result in mediated pathology without deleterious pro-oxidant side reactions which comprises administering an extract of the fruit of the Emblica officinalis plant to effect such advantageous result, preferably in a use formulation at an active use level of 0.005 to 5% by weight of the formulation.

8 Claims, No Drawings

METHOD OF BLOCKING FREE RADICAL PROCESSES WHICH RESULT IN MEDIATED PATHOLOGY WITHOUT DELETERIOUS PRO-OXIDANT SIDE REACTIONS

CROSS REFERENCE TO RELATED CO-PENDING U.S. PATENT APPLICATIONS

This application is a continuation-in-part of U.S. patent applications Ser. No. 09/251,917, filed Feb. 17, 1999, now U.S. Pat. No. 6,124,268 and Ser. No. 09/503,899, filed Feb. 15, 2000, now U.S. Pat. No. 6,235,721 by the same inventor as herein.

BACKGROUND OF THE INVENTION

1. Field of the Invention

This invention relates to a method of blocking free radical processes in an animal which result in mediated pathology without accompanying deleterious pro-oxidant side reactions, and, more particularly, to administration of an extract of the fruit of the Emblica officinalis plant to effect such result.

2. Description of the Prior Art

The biomedical literature has recognized that "free radicals" and other reactive species are involved in different human diseases. These species have been implicated in over 100 disorders, ranging from rheumatoid arthritis and haemorragic shock to cardiomyopathy and cystic fibrosis to gastrointestinal ischaemia, AIDS and even male pattern baldness. Some of the clinical conditions in which the involvement of free radicals is given in Table 1 below.

TABLE 1

| Category | Examples |
| --- | --- |
| Inflammatory/immune injury | Glomerulonephritis, vasculitis, Autoimmune diseases, rheumatoid arthritis, hepatitis |
| Ischaemia-reflow states | Stroke, myocardial infarction/arrythmias/angina/stunning, organ transplantation, inflamed rheumatoid joint, frostbite, Dupuytren's contracture, cocaine-induced fetal damage |
| Iron overload (tissue and plasma) | Idiopathic haemochromatosis, dietary iron overload (Bantu), thalassaemia and other chronic anaemias treated with multiple blood transfusions, nutritional deficiencies (kwashiorkor), alcoholism, multi-organ failure, cardiopulmonary bypass, fulminant hepatic failure, prematurity, alcohol-related iron overload, cancer chemotherapy/radiotherapy |
| Radiation injury | Consequences of nuclear explosions, accidental exposure, radiotherapy or exposure to hypoxic cell sensitizers or radon gas; cataract |
| Ageing | Disorders of premature ageing, ageing itself, age-related diseases, e.g. cancer |
| Red blood cells | Phenylhydrazine, primaquine and related drugs, lead poisoning, protoporphyrin photoxidation, malaria, sickle cell anaemia, favism, Fanconi's anaemia, haemolytic anaemia of prematurity, chemotherapy |
| Respiratory tract | Effects of cigarette smoke, snuff inhalation, other smoke inhalation, emphysema (COPD), hyperoxida, bronchopulmonary dysplasia, exposure to air pollutants (03, $NO_2$, $SO_2$ diesel exhaust), ARDS, mineral dust pneumoconiosis, asbestos carcinogenicity, bleomycin toxicity, paraquat toxicity, skatole toxicity, asthma, cystic fibrosis |

TABLE 1-continued

| Category | Examples |
| --- | --- |
| Heart and cardiovascular System | Alcohol cardiomyopathy, Keshan disease (selenium deficiency), artherosclerosis, anthracycline cardiotoxicity, cardiac iron overload |
| Kidney | Autoimmune nephrotic syndromes, aminoglycoside nephrotoxicity, heavy metal nephrotoxicity (Pb, Cd, Hg), myoglobin/haemoglobin damage, haemodialysis, transplant storage/rejection |
| Gastrointestinal tract | Betel nut-related oral cancer, liver injury caused by endotoxins or halogenated hydrocarbons (e.g. bromobenzene, $CCl_4$), exposure to diabetogenic agents, pancreatitis, NSAID-induced gastrointestinal tract lesions, oral iron poisoning |
| Brain/nervous system/ Neuromuscular disorders | Hyperbaric oxygen, vitamin E deficiency, exposure to neurotoxins, Alzheimer's disease, Parkinson's disease, Huntington's chorea, stroke, neuronal ceroid lipofuscinoses, allergic encephalomyelitis, aluminium overload, sequelae of traumatic injury, muscular dystrophy, multiple sclerosis, amyotrophic lateral sclerosis, Guam dementia; may also occur during preservation of fetal dopamine-producing cells for transplantation |
| Eye | Cataract, ocular haemorrhage, degenerative retinal damage/macular degeneration, retinopathy of prematurity (retrolental fibroplasia), photic retinopathy, penetration of metal objects |
| Skin | UV radiation, thermal injury, porphyria, hypericin, exposure to other photosensitizers, contact dermatitis, baldness |

Abbreviations: ARDS, adult respiratory syndrome; COPD, chromic obstructive pulmonary disease; NSAID, non-steroidal anti-inflammatory drug These pathologies have been alleviated with antioxidants which function as blockers of such radical process. However, an antioxidant cannot distinguish between radicals that play a useful physiologic role and those that are harmful. Moreover, antioxidant compounds not only function as antioxidants, but they may have pro-oxidant action as well. Examples of antioxidants which also exhibit pro-oxidant activity are given below:

Vitamin C

Vitamin C is a hydrophilic vitamin with well-known antioxidant properties; however Vitamin C also can act as a pro-oxidant in the following manner. Specifically, the combination of Vitamin C with $Fe^{3-}$ or $Fe^{2+}$ ions causes intense oxidation of polyunsaturated fatty acids (PUFAs). The mechanism of such pro-oxidation is as follows:

The Vitamin C radical (dehydroascorbate radical anion, Vit C.), a relatively non-reactive species, can decay by disproportionation resulting in the production of Vitamin C and dehydroascorbate (DHA), thereby terminating the propagation of free radical reactions:

$$2\text{Vit C.} + 2H^+ \rightarrow \text{Vit C} + \text{DHA}$$

Alternately, the vitamin C radical may reduce another $Fe^{3+}$ ion:

$$\text{Vit C.} + Fe^{3+} \rightarrow DHA + Fe^{2+}$$

During oxidation of Vitamin C, $H_2O_2$ is also formed:

$$\text{Vit C} + O_2 \rightarrow DHA + H_2O_2$$

The reduction of $Fe^{3+}$ thus appears to be the probable cause for the pro-oxidant action of Vitamin C. The degree of ferric ion reduction may therefore determine the prevalence of Vitamin C acting either as an antioxidant or as a pro-oxidant.

Vitamin E

The propagation reaction of the oxidative breakdown of PUFAs, indicated as LH, is shown below, where $K_1$ is the equilibrium constant:

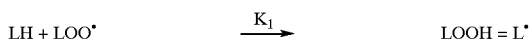

$$LH + LOO^{\bullet} \xrightarrow{K_1} LOOH = L^{\bullet}$$

In which $LOO^{\bullet}$ indicates lipid peroxyl radicals.

The lipid-soluble Vitamin E thus owes its antioxidant activity to trapping of $LOO^{\bullet}$, which in turn is reduced to stable LOOH (lipid hydroperoxides), as follows:

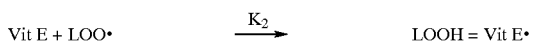

$$Vit\ E + LOO^{\bullet} \xrightarrow{K_2} LOOH = Vit\ E^{\bullet}$$

Vitamin E itself is a mixture of four lipid-soluble tocopherols (designated as α, β, γ and δ); α-tocopherol being the most active with respect to trapping of peroxyl radicals. The resonance stabilization of Vit E derived from α-tocopherol renders it less reactive than $LOO^{\bullet}$, therefore, Vitamin E is a good antioxidant.

In contrast, Vitamin E, if present at a relatively high concentration, can induce deleterious radical formation by a side reaction with LOOH, thus functioning also as a pro-oxidant.

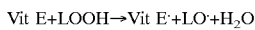

$$Vit\ E + LOOH \rightarrow Vit\ E^{\bullet} + LO^{\bullet} + H_2O$$

Superoxide Dismutase (SOD)

Intra-articular administration of Cu/Zn-containing SOD has been used to prevent free radical damage. However, $H_2O_2$, a reaction product of $O_2^-$ dismutation, can inactivate SOD. Therefore, in the presence of $H_2O_2$, SOD will act as a pro-oxidant.

Glutathione (GSH)

Thiol (SH) groups are essential in the protection against the deleterious effects of reactive oxygen species. The tripeptide GSH (γ-Glu-Cys-GLY) is the pivot in various protective systems. In addition, the SH group is important for the function of many proteins. To protect the SH groups of proteins, high concentrations of the reducing GSH are required. However, it is difficult to estimate the level of GSH needed for this function since thiols may exhibit both antioxidant and pro-oxidant actions. The pro-oxidant activity of the thiol GSH can be simply explained as involving the reduction of $Fe^{2+}$. Hence, a generally accepted antioxidant, such as GSH, may possess deleterious pro-oxidant activity under certain conditions.

Accordingly, it is an object of this invention to provide a method of blocking free radical processes which result in mediated pathology without deleterious pro-oxidant side reactions.

Another object of the present invention is to provide advantageous antioxidant activity to block free radical processes without accompanying pro-oxidant side reactions by administration of an extract of the fruit of the Emblica officinalis plant, optionally including one or more additional antioxidants.

A feature of the invention is the provision of a use formulation containing an active use level of said extract in the amount of about 0.005 to 5% by weight of said formulation.

These and other objects and features of the invention will be made apparent from the following description thereof.

SUMMARY OF THE INVENTION

What is described herein is a method of blocking free radical processes in an animal which result in mediated pathology without deleterious pro-oxidant side reactions. The method comprises administering an extract of the fruit of the Emblica officinalis plant to effect such advantageous result. In practice, a use formulation containing an active use level of said extract in an amount of about 0.005 to 5% by weight of the formulation, is utilized for such administration. Optionally one or more additional antioxidants may be included in the formulation.

DETAILED DESCRIPTION OF THE INVENTION

The antagonist for blocking free radical processes in humans according to the invention is an extract blend, hereinafter referred to as "Extract Blend (EB)", which is isolated in stable form from the fruit of the Emblica officinalis plant, as described in detail in U.S. Pat. No. 6,124,268. The extraction process includes treating the finely-pulped fruit with a dilute aqueous or alcoholic-water salt solution, e.g. a 0.1 to 5% (w/w) sodium chloride solution, or the like, preferably at about 70° C. ±5° C., or with a buffer solution, e.g. 0.1 to 5% (w/w) of sodium citrate/citric acid, or the like, filtering and drying, to provide the extract in powder form.

The extract includes the active constituents Emblicanin-A and -B, which are gallic/ellagic acid derivatives of 2-keto-glucono-δ-lactone, in an amount, by weight, of about 35–55%; as well as Punigluconic acid, or 2,3-di-O-galloyl-4,6-(S)-hexahydroxydiphenoyl gluconic acid (about 4–15%); Pedunculagin, or 2,3,4,6-bis-(S)-hexahydroxydiphenoyl-D-glucose (about 10–20%); Rutin, or flavanol-3-glycoside or 3',4',5,7-tetrahydroxy-flavone-3-)-rhamnoglucoside (about 5–15%); and low-to-medium molecular weight tannoids of gallic/ellagic acid (about 10–30%); gallic acid (about 0–5%) and ellagic acid (0–5%).

Experimental Results

1. Antioxidant Activity

Several test materials at concentrations of 2.5, 5, 10, 20, 40 and 80 μg/mL were separately added to a control, DPPH (diphenyl picryl hydrazyl) radical solution (100 μM in absolute ethyl alcohol) in a cuvette. After 20 minutes, the absorbance (optical density) of the mixture was measured at a wavelength of 570 nm and compared to that of the control sample. The degree of scavenging of the DPPH radical by each test sample was calculated by comparing the absorbance of the test sample and the diluent control reaction mixture. The results are shown in Table 2 below, a lower IC value indicating a better antioxidant effect on the DPPH radical.

TABLE 2

| Test Material | $IC_{50}$ (μg/mL)* |
|---|---|
| Ascorbic acid (AA) | 18.41 ± 3.88 |
| Pycnogenols (PG) (Marker) | 27.33 ± 4.44 |
| α-Tocopheryl acetate (TA) | 50.55 ± 7.03 |
| Extract Blend (EB) | 12.82 ± 2.01 |

TABLE 2-continued

| Test Material | IC$_{50}$ ($\mu$g/mL)* |
|---|---|
| EB + AA (1:1, w/w) | 8.88 ± 1.77 |
| EB + TA (1:1, w/w) | 10.22 ± 2.03 |

*Values are mean ± SEM (n = 10 to 12)

The results show that Extract Blend alone had a more pronounced antioxidant effect in controlling oxidation than any of the other antioxidant test compounds. Mixtures of EB and AA or TA also were significantly better than any of the individual compounds.

Exact Blend thus is a very potent antioxidant agent (and not a pro-oxidant) at all concentrations as evident from the reduction of DPPH radical to DPPH$_2$ under the Udenfriend reaction conditions. The mechanistic sequence of this reaction is shown below:

When ascorbic acid (AA) is in low concentration:

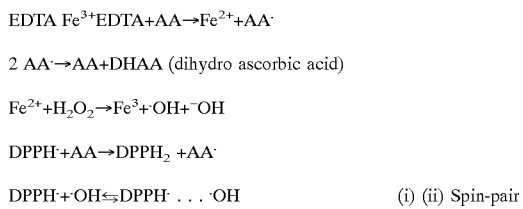

$$\text{DPPH}^-+\text{OH} \leftrightharpoons \text{DPPH}^- \ldots \text{OH} \qquad \text{(i) (ii) Spin-pair}$$

The decrease in absorbance observed herein is due to the shift in equilibrium to (I), which is indicated by the appearance of a new shoulder at a lower wavelength ($\lambda$~520 nm). DPPH$_2$+·OH [after dissociation as in (I)] to DPPH·+H$_2$O causes an increase in the optical density to 0.764.

When ascorbic acid is in high concentration:

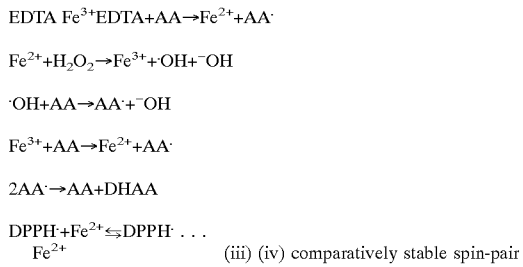

$$\text{DPPH}^-+\text{Fe}^{2+} \leftrightharpoons \text{DPPH}^- \ldots \text{Fe}^{2+} \qquad \text{(iii) (iv) comparatively stable spin-pair}$$

The appreciable decrease in the optical density value at $\lambda$570 nm is due to a shift in the equilibrium to (iv).

In the case of EB, there is a significant reduction in the optical density due to the formation of type (iv) spin-pair with Emblicanin-A resulting in further reduction of DPPH· to DPPH$_2$.

2. Polymerization of Methylmethacrylate (MMA) to Polymethytlmethacrylate (PMMA)

Scope of the Method

Soft spin radicals do not initiate/augment polymerization of MMA into PMMA. The fact that the pro-oxidant activity of AA at low concentrations is quite prominent is indicated by the significant augmentation of polymerization at low concentration of AA (1.0 mg)+H$_2$O$_2$ via the OH radical (Table 3). Thus, the pro-oxidant effect of a low concentration of AA could be systemically quite dangerous due to distinct involvement of OH radicals. This determination supports the superior antioxidant effect of EB under all circumstances.

Method

MMA (1 ml, ~980 mg) was added to a solution of ferrous sulfate (15 mg) in double distilled water. N$_2$ was passed through the mixture for 30 min. followed by H$_2$O$_2$. The onset of polymerization (the induction period in minutes) was noted. Polymerization was completed in about 24 hours at 35±2° C. The resulting precipitate was collected, washed and dried at 50° C. until a constant weight was obtained (See Table 3).

TABLE 3

Polymerization of Methylmethacrylate to Polymethylmethacrylate in Presence or Absence of Extract Blend (EB) or Ascorbic Acid by Fenton's Reagent

| Sample | Induction Time (in Min.) | Yield of PMMA (in MG.) | % Conversion of MMA → PMMA |
|---|---|---|---|
| Control | 0 | 668 | 68.1 |
| +AA (1 mg) | 0 | 772 | 78.7↑ |
| +AA (2 mg) | 0 | 692 | 69.8↑ |
| +AA (3 g) | 0 | 670 | 68.2↑ |
| +AA (4 mg) | 0 | 432 | 44.0 |
| +AA (5 mg) | 0 | 227 | 23.1 |
| +AA (10 mg) | 0 | 83 | 8.4 |
| +EB (1 mg) | 20 | 124 | 12.6↓ |
| +EB (2 mg) | 65 | 62 | 6.3↓ |
| +EB (3 mg) | 120 | Traces | <1 ↓ |
| +EB (4 mg) | >5 hr | 0 | 0 |
| +EB (5 mg) | >5 hr | 0 | 0 |
| +AA +EB (1 + 1 mg) | 130 | 44 | 4.4 |
| +AA +EB (1 + 2 mg) | 138 | 22 | 2.2 |
| +AA +EB (1 + 3 mg) | >5hr | 0 | 0 |

Low concentrations of ascorbic acid thus augmented polymerization of MMA→PMMA (via ·OH radical; pro-oxidant activity), whereas EB, either significantly inhibited (1–3 mg), or totally prevented (4–5 mg) the polymerization reaction. The induction time of polymerization in the presence of EB thus is significantly higher than that of ascorbic acid which is instantaneous. Mixtures of EB and AA actually reversed the pro-oxidant activity of AA at low concentrations Accordingly, EB is a very potent antioxidant agent at all concentrations and devoid of pro-oxidant activity.

3. Prevention of DNA Strand Scission

The DNA strand scission was investigated by a method published by T. Ozawa, et al [Biochem. Mol. Biol. Int. 31, 455–46, 1993]. The method consists of addition of hydrogen peroxide (30%, final concentration 25 mM) to a mixture of Cu(en)$_2$ (final concentration 0.25 mM) and 0.5 mcg of PBR 322 plasmid DNA solution (Takara Co., Japan). The hydroxyl radical, generated from Cu(en)$_2$-hydrogen peroxide reaction, caused DNA strand scission.

At physiological pH, EB significantly suppressed the DNA strand-scission by hydroxyl radicals produced from the reaction of Cu(en)$_2$ and hydrogen peroxide. Both Vitamin C and a blend of Vitamins C/E (1:30), w/w) accelerated DNA strand-scission compared to the control value (Table 4). The protective effect of EB is due to: (1) Captodative action on the generation of hydroxyl radical by chelation of Cu ions from a Cu(en)$_2$-complex. In contrast, both Vitamin C and a blend of Vitamins C/E produced loose and partially chelated Cu ions, which, by an Udenfriend-type reaction, further accelerated the DNA strand-scission (Table 4). The importance of DNA strand-scission in cellular damage is well known. EB thus helps to maintain the integrity of DNA against oxidative stress. It is well documented that Vitamin E, also under certain conditions, also acts as a pro-oxidant. Hence, the augmentation of DNA strand-scission (instead of protection) by Vitamin C/E blend is self-explanatory.

TABLE 4

Comparative Suppressive Effects of DNA Strand Scission

| TYPES OF DNA | \multicolumn{5}{c}{Test Run} | | | | |
|---|---|---|---|---|---|
| | 1 | 2 | 3 | 4 | 5 |
| Native form of Supercoiled DNA (SC) | 90 | — | 80 | 5 | — |
| Open circular form Of DNA (OC) | 10 | 60 | 20 | 65 | 40 |
| Linear form of DNA (LIN, Produced after breakage) | — | 40 | — | 30 | 60 |

Test Run
1. DNA alone (without OH radical). Note: LIN absent and OC is intermediate to LIN
2. DNA + OH radical [from $Cu(en)_2$-hydrogen peroxide)
3. DNA + OH radical + EB. Note: LIN absent and OC is only 20%
4. DNA + OH radical + Vitamin C/E blend. Note: Depletion of SC concentration
5. DNA + OH radical + Vitamin C. Note: Significant increase in LIN value indicative of DNA strand scission.

The extract blend may be administered to an animal such as a human in a use formulation containing about 0.005 to 5% by weight of the formulation. Optionally other known antioxidants, such as ascorbic acid, tocopherols, pycnogenols, glutathione, and the like, may be included in the formulation.

Suitable use formulations may be in the form of tablets, syrups, elixirs, lotions, cremes or gels, and administered for pharmaceutical, nutritional or personal care applications. Pharmaceutical formulations preferably are in the form of tablets, syrup, elixir or capsules while personal care compositions for skin care, for example are solutions, lotions, crème or gel.

While the invention has been described with particular reference to certain embodiments thereof, it will be understood that changes and modifications may be made which are within the skill of the art. Accordingly, it is intended to be bound only by the following claims, in which:

What is claimed is:

1. A method of blocking free radical processes in an animal without accompanying deleterious pro-oxidant side reactions which comprises administering an extract blend of the fruit of the Emblica officinalis plant to the animal.

2. A method according to claim 1 wherein said extract blend includes Emblicanin-A and B.

3. A method according to claim 2 wherein said extract blend comprises, by weight, (1) and (2) about 35–55% of the gallic/ellagic acid derivatives of 2-keto-glucono-δ-lactone; (3) about 4–15% of 2,3-di-O-galloyl-4,6-(S)-hexahydroxydiphenoylgluconic acid; (4) about 10–30% of 2,3,4,6-bis-(S)-hexahydroxydiphenoyl-D-glucose; (5) about 0–15% of 3',4',5,7-tetra-hydroxyflavone-3-O-rhamnoglucoside; and (6) about 10–30% of tannoids of gallic/ellagic acid.

4. A method according to claim 3 wherein said extract blend also includes about 0–5% of gallic acid and about 0–5% of ellagic acid.

5. A method according to claim 1 wherein one or more additional antioxidants are included with said extract blend.

6. A method according to claim 5 wherein said antioxidant is selected from ascorbic acid, tocopherols and glutathione.

7. A formulation for blocking free radical processes in an animal without accompanying deleterious pro-oxidant side reactions which comprises, by weight, about 0.005 to 5% of an extract blend of the fruit of the Emblica officinalis plant.

8. A formulation according to claim 7 for blocking such processes in a human, which also includes one or more additional antioxidants.

* * * * *